(12) United States Patent
Butler

(10) Patent No.: US 8,731,713 B2
(45) Date of Patent: May 20, 2014

(54) PRESCRIPTION DISPENSING SYSTEM

(76) Inventor: C. David Butler, Manchester, MO (US)

( * ) Notice: Subject to any disclaimer, the term of this patent is extended or adjusted under 35 U.S.C. 154(b) by 2202 days.

(21) Appl. No.: 11/422,484

(22) Filed: Jun. 6, 2006

(65) Prior Publication Data

US 2007/0293983 A1   Dec. 20, 2007

(51) Int. Cl.
*G06F 17/00* (2006.01)
(52) U.S. Cl.
USPC .......................................... 700/244; 700/237
(58) Field of Classification Search
USPC ................................................. 700/237, 244
See application file for complete search history.

(56) References Cited

U.S. PATENT DOCUMENTS 6,711,460 B1 *  3/2004  Reese ........................... 700/244

* cited by examiner

*Primary Examiner* — Timothy Waggoner

(57) ABSTRACT

A prescription dispensing system having a dispensing station for holding an inventory of prescription medications, a secure internet connection to the dispensing station for access by a potential prescription medication recipient, by healthcare personnel in a physician office and by pharmacy personnel at the pharmacy distribution center in a remote location, at least two webcams for visual and auditory communication between the location of the dispensing station and the pharmacy personnel via the internet to allow identification of the correct medication, identification and communication with the correct potential prescription medication recipient, and visual validation and recording of all documentation from the physician's office or potential prescription medication recipient, and a biometric reader disposed at the dispensing station for identifying a potential prescription medication recipient. The system may include various enhancements to allow accurate dispensing of the proper medication and direct secure internet communication between the pharmacist and the authorized recipient of the medication.

46 Claims, 4 Drawing Sheets

PRESCRIPTION DISPENSING SYSTEM

FIELD OF THE INVENTION

This invention relates generally to systems for dispensing prescription drugs, and more particularly to such systems that are usable in physicians' offices.

BACKGROUND OF THE INVENTION

Obtaining the proper medication is frequently a time-consuming, inefficient, and expensive process. The physician diagnoses an ailment, frequently at the physician's office, and the often-sick patient is then required to carry a handwritten, sometimes illegible, paper prescription to an often-distant grocery store, discount store or chain pharmacy to have it filled. Each of these steps underutilizes expensive professionals due to inefficient operations and administration.

Attempts to simplify this process are often stymied, however, by the necessary regulation of the dispensing of prescription medications. State and federal law requires the involvement of a registered pharmacist before the medication is provided to the patient (or other person retrieving the medication on behalf of the patient). Most physician's offices do not have a pharmacist at hand, so the trip to a pharmacy of some sort to obtain the actual medication has heretofore been necessary.

SUMMARY OF THE INVENTION

Among the various objects of the present invention may be noted the provision of a prescription dispensing system that makes most medications immediately available at the physician's office.

Another object is the provision of such a system that complies with all relevant laws and regulations concerning the dispensing of prescription medications.

A third object is the provision of such a system that multiplies the effectiveness of pharmacists.

A fourth object is the provision of such a system that allows a pharmacist to verify the medication being dispensed from a plurality of different locations.

A fifth object is the provision of such a system that identifies, selects and counts the correct medication, identifies the correct patient, offers drug information to the patient, and provides pharmacist/patient interaction at a plurality of different locations.

A sixth object is the provision of such a system that notifies the pharmacist of potential drug interactions based upon the patient's record.

A seventh object is the provision of such a system which uses biometrics to identify the patient or authorized medication recipients.

An eighth object is the provision of such a system which places the medication in a properly labeled vial before dispensing to the patient or authorized medication recipient.

A ninth object is the provision of such a system which allows the pharmacist to verify the accuracy of the label.

A tenth object is the provision of such a system which provides audio and visual communication between the pharmacist and the patient or authorized medication recipient.

An eleventh object is the provision of such a system which allows the patient or authorized medication recipient to pay for the medication at the physician's office.

A twelfth object is the provision of such a system which facilitates the refilling of prescriptions at physician's offices.

A thirteenth object is the provision of such a system that promotes improved health treatment, since treatment can start immediately under physician supervision.

A fourteenth object is the provision of such a system that provides improved communications between the physician personnel, pharmacy personnel, and the patient, thereby reducing the chance for incorrect or inappropriate prescriptions.

A fifteenth object is the provision of such a system that provides improved monitoring of refills by the physician.

Other objects and features will be in part apparent and in part pointed out hereinafter.

Briefly, the prescription dispensing system of the present invention includes a dispensing station for holding an inventory of prescription medications, a secure internet connection to the dispensing station for access by a potential prescription medication recipient, by healthcare personnel in a physician office and by pharmacy personnel at the pharmacy distribution center in a remote location, at least two webcams for visual and auditory communication between the location of the dispensing station and the pharmacy personnel via the internet to allow identification of the correct medication, identification and communication with the correct potential prescription medication recipient, and visual validation and recording of all documentation from the physician's office or potential prescription medication recipient, and a biometric reader disposed at the dispensing station for identifying a potential prescription medication recipient, said biometric reader being connected via the secure internet connection to the remote location. If desired, the system can include numerous other features such as at least three webcams, disposed in the physician office, as well as inside and outside the dispensing station, further including a microphone, monitor and speaker outside the dispensing station, holding prescription medications in inventory in the dispensing station in barcoded containers specific to each medication, barcoded modules containing an updateable, specified combination of medication containers for said dispensing station's inventory, means for comparing the image of dispensed medication with a database of correct images for said medications, means for comparing the medication prescribed with a patient prescription record as entered by healthcare personnel in the physician's office or by pharmacy personnel at the pharmacy distribution center, apparatus for counting out the prescribed medication, transferring said medication to the vial, applying a label to the vial, and transferring the visually inspected container to the prescription medication recipient, under visual monitoring by the pharmacy personnel via one of said webcams, a magnetic card reader disposed at the dispensing station for reading cards selected from the group consisting of smart cards, payment cards, and third-party reimbursement cards, a webcam, microphone, barcode reader, computer and monitor for the pharmacy personnel at the remote location for allowing visual and barcode verification of all barcoded containers, visual verification of the medication, container and labeling, and visual and verbal verification of the patient/customer, physician and written documentation, and the like.

BRIEF DESCRIPTION OF THE DRAWINGS

Similar reference characters indicate similar parts throughout the several views of the drawings.

DESCRIPTION OF THE PREFERRED EMBODIMENT

Figure 1:
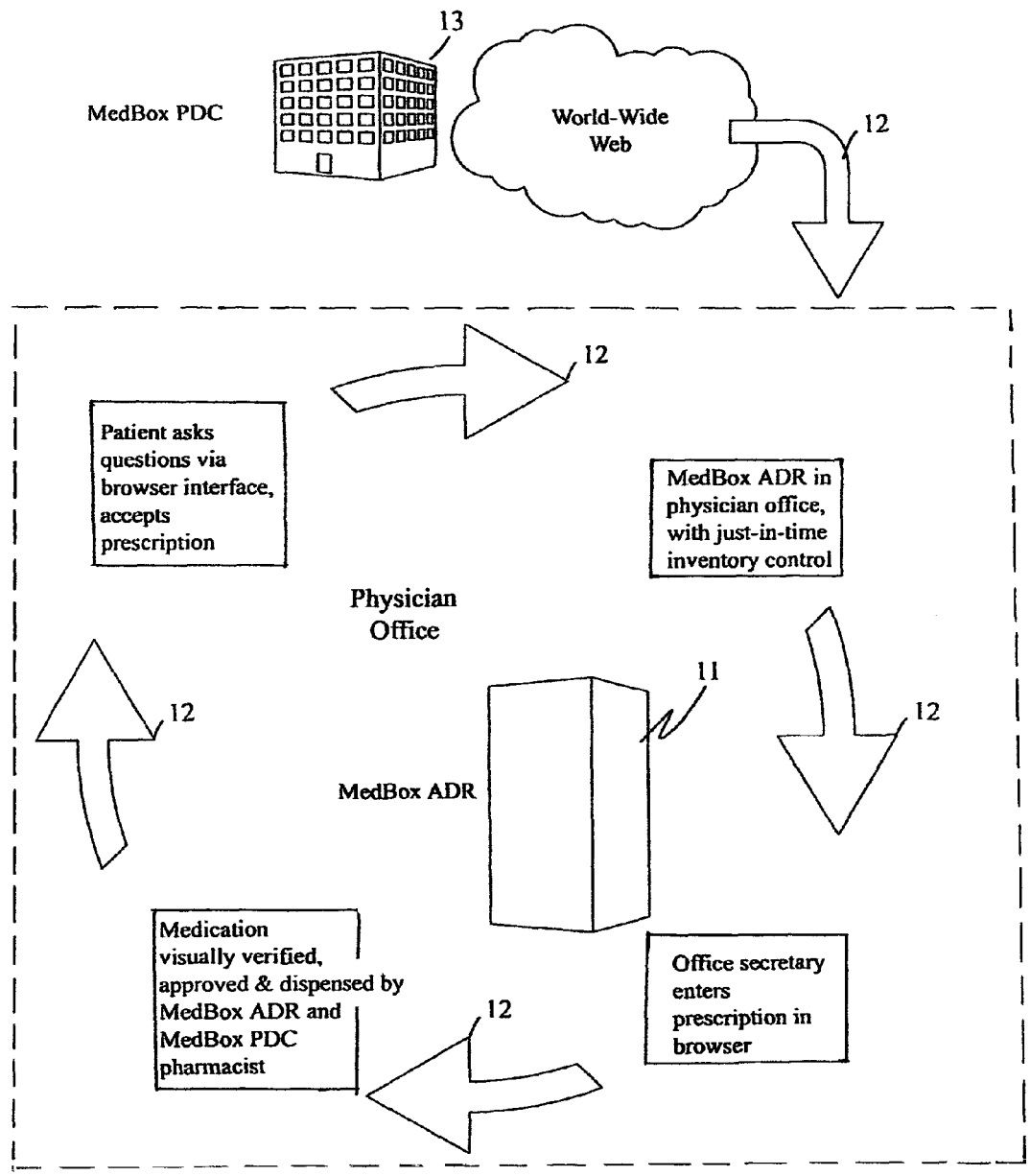
FIG. 1 is a schematic view of the operation of the system of the present invention.

Turning to the drawings, a schematic of the present system (FIG. 1) includes a dispensing station 11 for holding an inventory of prescription medications. The dispensing station is preferably disposed in a physician's office or similar convenient location. The dispensing station 11 is connected via a secure internet connection 12 to a pharmacist (pharmacy personnel) at a remote location 13 (called a pharmacy distribution center or PDC). It should be realized that the pharmacy distribution center may or may not also be a location at which prescription medication are stored prior to being supplied to dispensing station 11 (or any of a number of additional dispensing stations not shown). The secure internet connection provides access not only between the patient (or authorized medication recipient) and the pharmacist, but also between those parties and the physician office personnel such as the physician, nurses, and record keepers. For example, the physician office secretary (or other personnel at the physician office) may enter the prescription in a browser for submission to the PDC. In FIG. 1, various steps performed in connection with the present invention are shown in a box, and the steps and components usually performed or located in the physician's office are surrounded by dashed lines. For example, the dispensing station 11, shown in "MedBox ADR" in FIG. 1, is located in the physician's office and indicated by the enclosed box, and is reloaded as needed by just-in-time inventory control. Similarly, FIG. 1 shows that the the office secretary in the physician's office can enter the prescription in a browser using the secure internet connection. The medication for that prescription is visually verified, approved and dispensed by the MedBox ADR 111 and by MedBox PDC pharmacist at location 13. The patient may ask question via the browser interface and the secure internet connection 12, and accepts the prescription.

Figure 2:
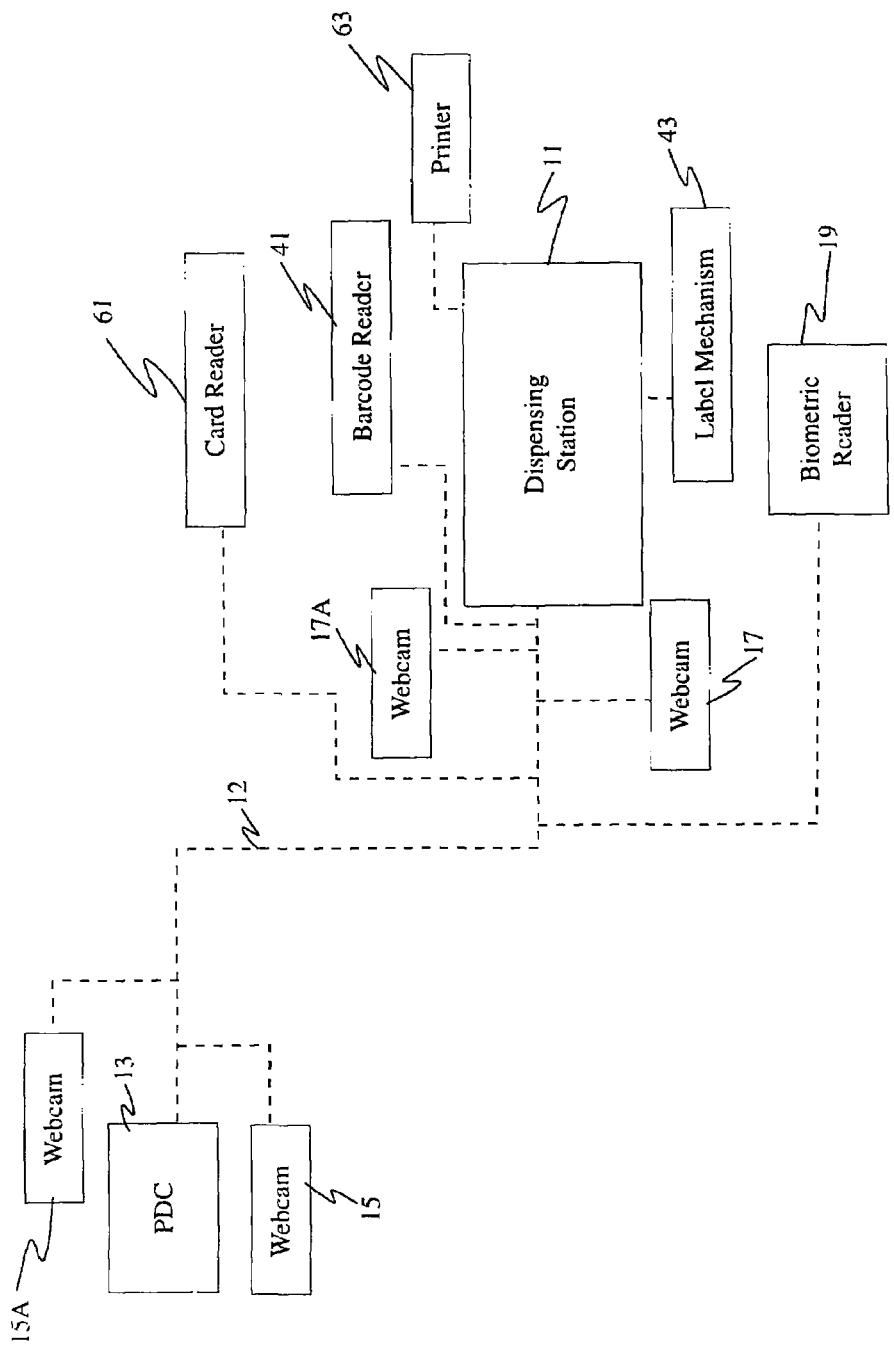
FIG. 2 is a block diagram of various components of the system of the present invention.

The system of the present invention also includes at least two webcams 15, 17 (see FIG. 2) for visual and auditory communication between the location of the dispensing station 11 and the pharmacy personnel at PDC 13 via the internet to allow identification of the correct medication, identification and communication with the correct potential prescription medication recipient, and visual validation and recording of all documentation from the physician's office or potential prescription medication recipient. As is explained below, it is preferred that the system include two additional webcams 15A and 17A. In the four webcam system, two webcams 15, 15A are disposed at the PDC, and two (17, 17A) are disposed at dispensing station 11. These allow the pharmacist to review the medication prior to dispensing, allow the pharmacist to visually identify the patient or authorized medication recipient, and allow the pharmacist and patient or authorized recipient to teleconference concerning the medication.

The system also includes a biometric reader 19 disposed at the dispensing station for identifying a potential prescription medication recipient. The biometric reader is preferably connected via the secure internet connection to the PDC 13.

The dispensing station 11 is preloaded with an inventory of medication that matches a profile of usually dispensed medications for that office. The actual dispensing of medication requires two inputs, however. The first, from the healthcare personnel in the physician office represents an amount and type of medication for a patient. The second, from the pharmacist at the PDC 13 is an authorization signal to dispense a vial of medication. Prior to providing the authorization signal (via the secure internet connection, for example), the pharmacist uses one of the webcams to obtain visual verification of the amount and type of medication inserted into the vial prior to authorization to dispense.

Figure 4:
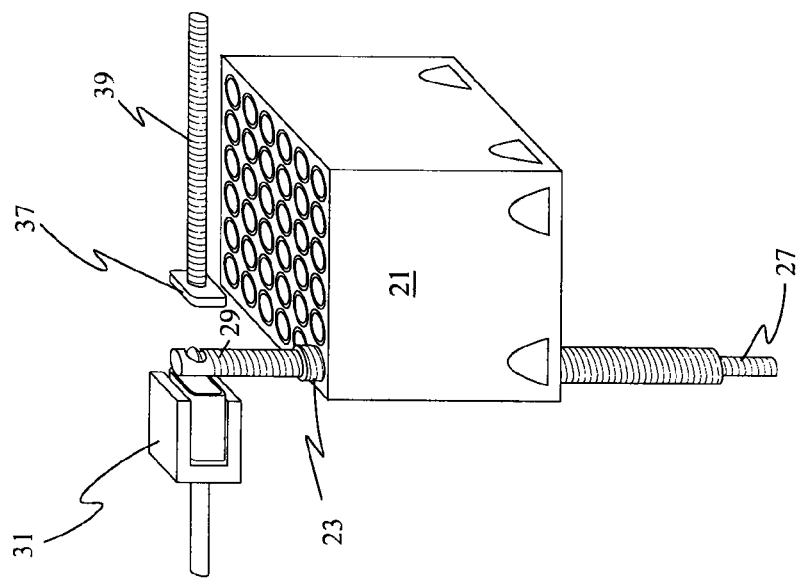
FIGS. 3 and 4 illustrate the dispensing of medication by the system of the present invention.
Figure 3:
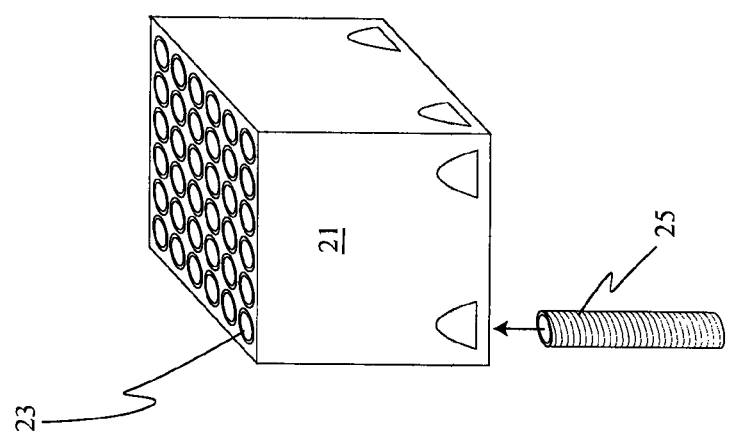

Dispensing station 11 (see FIGS. 3 and 4) includes a tube holder 21 containing a plurality of medication tubes 23 (only one of which is shown in FIGS. 3 and 4). An externally threaded shaft 25 under software control is used to raise the desired medication tube 23 to the position shown in FIG. 4. A drive system including an internally threaded shaft 27 is then used to push the medical tablets up at a metered rate and amount as indicated at 29. A vial holder 31 is used to hold vial 33 in a position for receiving the medication, one tablet at a time. For example, holder 31 may hold vial 33 vertically above the medication as it is forced upwardly by threaded shaft 27. Preferably the vial 33 is sealed to the medication tube 23 during the transfer process to provide a closed system. Once the desired amount is dispensed into vial 33, holder 31 is moved to the position shown in FIG. 4 so that a vial top 37 may be screwed onto the vial by another threaded shaft 39. For this purpose, the vial may be internally threaded and the top 37 may have a slot formed therein. Of course, any number of different mechanisms may be used to dispense the desired amount of medication into the vial and any number of different attachment mechanisms may be used to secure the top 37 to vial 33. Such dispensing and attachment mechanisms are well-known in the art. Movement of the medication horizontally, vertically, or a combination thereof are all within the scope of the present invention.

It is preferred that one of webcams 17, 17A is used to allow the pharmacist to visually observe the transfer of the medication to vial 33, and to visually verify the identity of the medical being dispensed. Preferably a barcode reader 41 (FIG. 2) is also present at the dispensing station 11. Each medication tube 25 may be marked with a barcode, if desired, to identify the medication contained therein. Barcode reader 41 then allows the system to verify that the medication being dispensed is the same as the medication being prescribed. The dispensing station has a label printing and applying mechanism 43 associated therewith to print and apply a label to vial 33. Such label contains all the information required by the relevant state pharmacy authority, including the type and amount of medication inserted into the vial.

In those cases where the medication is liquid, the liquid medication may be stored in the dispensing station in predetermined units, or it may be stored in syringes connected by suitable tubing for dispensing of a desired amount into a container, as prescribed by the physician.

It should be appreciated that the present system allows a small number of pharmacists at PDC 13 to handle the dispensing of medication from a large number of dispensing stations 11 disposed at a potentially equally large number of different locations. The pharmacist or pharmacists at PDC 13 have access to the patient medication record corresponding to a prescription to be dispensed and having access to the webcams to verify the type and amount of medication dispensed, for each prescription. It is preferred that healthcare personnel at the physician's office supply biometric information to the dispensing station corresponding to the potential prescription medication recipient (patient or other authorized recipient) and that the biometric reader 19 provide this information to the system and/or to the dispensing pharmacist for verification. Such a biometric reader could be a fingerprint reader, for example.

Figure 5:
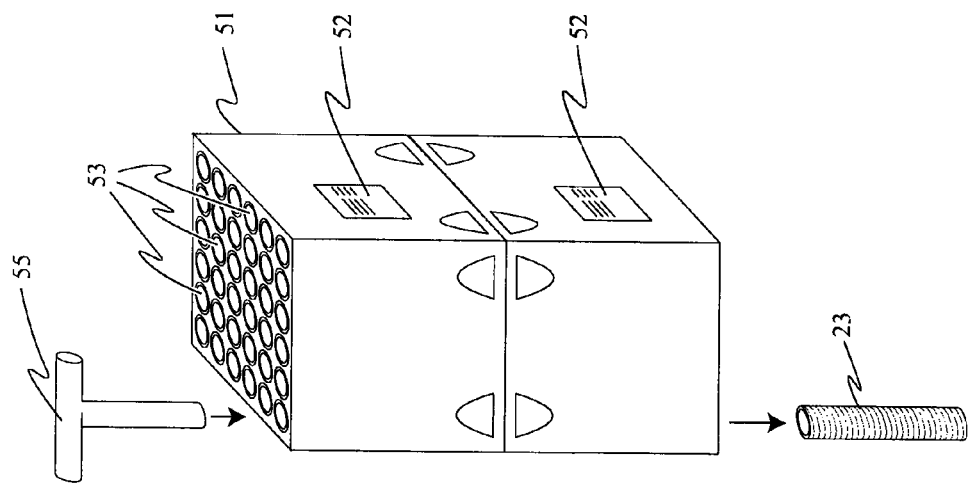
FIG. 5 illustrates the reloading of medication in a dispensing station used in the system of the present invention.
Figure 5:
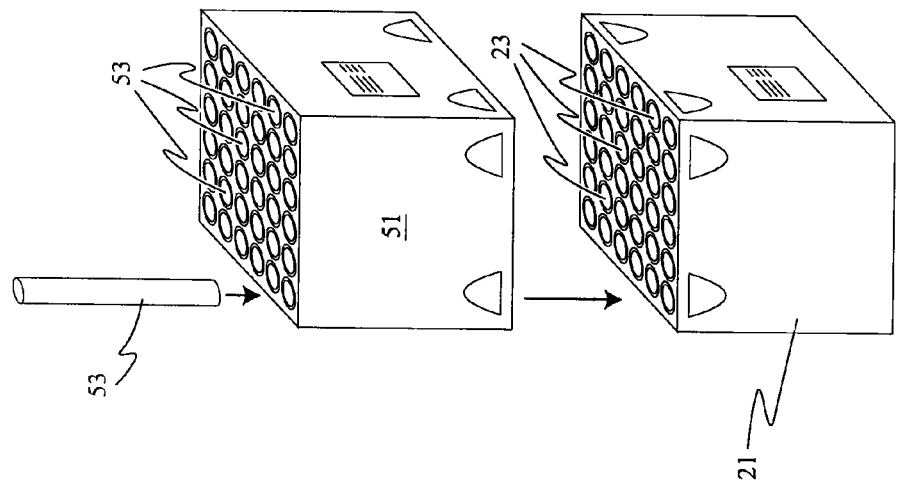

Turning to FIG. 5, there is illustrated the loading of the medications for a particular dispensing station 11. The medications fitting the profile for a particular physician's office are loaded into a module 51 at PDC 13 (or at some other suitable location). More specifically, the pharmacy technician checks the inventory for each dispensing station 11, and from that information loads the medication tubes for module 51 for that specific dispensing station. It is preferred that these modules 51 are bar-coded (as at 52) to ensure that the proper medication is provided to the proper location. At the physical location of that specific dispensing station 11, the refilling module 51 is placed adjacent the medication tube holder 21 corresponding to that location (as shown in the rightmost portion of FIG. 5). The bar code match is verified. The medication tubes 53 from the refilling module are then moved into holder 21 by a suitable tool 55 and the preexisting medication tubes 23 are removed. After this operation is completed, dispensing station again contains the kind and amount of medication that fits the profile for that location.

As described above, the present system allows for direct communication (via the internet) between the patient (or authorized medication recipient), the pharmacist, and the healthcare personnel at the physician's office. This communication is accomplished via the webcams, microphones, speakers and monitors, via the secure internet connection. It allows the healthcare personnel at the physician's office to introduce the patient (or medication recipient) to the pharmacist, allows the pharmacist to identify the person at the dispensing station 11, and allows the patient or other authorized medication recipient to ask questions (and receive answers) about medication-related issues, all in a confidential manner that satisfies all medical privacy requirements, such as HIPAA requirements. This pharmacist/patient interaction is also sufficient to satisfy state board of pharmacy regulations regarding pharmacist counseling and provision of drug information within the state where the dispensing station is located.

The webcams may also be used to transmit an official copy of the written prescription to the pharmacist at PDC 13. (Alternatively, the prescription may be transmitted electronically to the pharmacist by means of a web-based form, or via traditional fax or paper forms, completed by healthcare personnel at the physician's office.) Webcams also allow the image of dispensed medication to be compared with a database of correct images for the prescribed medications to further insure that the correct medication is being dispensed. The system also automatically compares the medication being dispensed with the patient prescription record as entered by healthcare personnel in the physician's office or by pharmacy personnel at the pharmacy distribution center to further prevent error.

Of course, the webcams may also be used to transmit a copy of payment documents to PDC 13, such as copies of credit or debit cards, third-party cards, or forms. Alternatively, dispensing station 11 may also have associated therewith a card reader 61 for directly acquiring payment card information via the secure internet connection.

It is also preferred that the system include a printer 63 associated with the dispensing station 11 to provide printed material to the patient or other authorized medication recipient regarding the dispensed medication as required by state board of pharmacy regulations within the state where the dispensing station is located.

From the above it will be seen that the various objects and features of the present invention are achieved and other advantageous results obtained. The foregoing description of the present invention is by way of illustration only, and is not to be used in limiting the scope of the invention in any way.

What is claimed is:

1. A prescription dispensing system comprising:
    a dispensing station for holding an inventory of prescription medications;
    a secure internet connection to the dispensing station for access by a potential prescription medication recipient, by healthcare personnel in a physician office and by pharmacy personnel at the pharmacy distribution center in a remote location;
    at least two webcams for visual and auditory communication between the location of the dispensing station and the pharmacy personnel via the internet to allow identification of the correct medication, identification and communication with the correct potential prescription medication recipient, and visual validation and recording of all documentation from the physician's office or potential prescription medication recipient;
    a biometric reader disposed at the dispensing station for identifying a potential prescription medication recipient, said biometric reader being connected via the secure internet connection to the remote location, wherein the dispensing station is located in a physician office and the dispensing station inventory matches a profile of usually dispensed medications for said office.

2. The prescription dispensing system as set forth in claim 1 wherein the dispensing station is responsive to a prescription signal from the healthcare professional in the physician office representing an amount and type of medication for a patient to insert said amount of medication of the specified type into a vial.

3. The prescription dispensing system as set forth in claim 2 wherein the dispensing station dispenses said vial of medication upon receipt of an authorization signal from the pharmacist at the remote location.

4. The prescription dispensing system as set forth in claim 3 wherein one of the webcams supplies to the pharmacist a visual verification of the amount and type of medication inserted into said vial prior to authorization to dispense.

5. The prescription dispensing system as set forth in claim 2 wherein the dispensing station includes a tube containing said medication and a drive system for moving predetermined amounts of said medication into said vial.

6. The prescription dispensing system as set forth in claim 5 wherein said drive system drives the medication into said vial one unit of medication at a time.

7. The prescription dispensing system as set forth in claim 5 wherein the tube containing said medication is sealed to the vial during insertion of the medication from the tube into the vial.

8. The prescription dispensing system as set forth in claim 5 wherein the drive system is disposed to move the medication horizontal from the tube to the vial.

9. The prescription dispensing system as set forth in claim 5 wherein the drive system is disposed to move the medication linearly from the tube to the vial.

10. The prescription dispensing system as set forth in claim 9 wherein the drive system is disposed to move the medication vertically before it is moved linearly from the tube to the vial.

11. The prescription dispensing system as set forth in claim 5 wherein the drive system operates under visual observation by the pharmacist via one of the webcams.

12. The prescription dispensing system as set forth in claim 5 wherein the tube includes a barcode label identifying the medication contained therein.

13. The prescription dispensing system as set forth in claim 12 wherein the dispensing station includes a barcode reader to insure that the medication being disposed corresponds to the medication prescribed.

14. The prescription dispensing system as set forth in claim 2 wherein the dispensing station includes means for providing a state board of pharmacy approved label on the vial, said label including information concerning the type and amount of medication inserted into the vial and all labeling requirements of the state within which the prescription dispensing system is located.

15. The prescription dispensing system as set forth in claim 14 wherein the vial includes a flat surface for said label.

16. The prescription dispensing system as set forth in claim 2 wherein said dispensing station includes means for attaching a top to the vial after the medication is inserted into the vial.

17. The prescription dispensing system as set forth in claim 16 wherein the vial is threaded to receive said top.

18. The prescription dispensing system as set forth in claim 16 wherein said top includes an external slot to facilitate manual removal thereof to obtain access to the medication.

19. The prescription dispensing system as set forth in claim 2 wherein the medication is liquid, said liquid medication being stored in the dispensing station in predetermined units.

20. The prescription dispensing system as set forth in claim 5 wherein the medication is liquid, and the liquid medication is stored in syringe-like tubes connected by tubing to the drive system to allow the drive system to deliver the volume of liquid medication as prescribed by the physician.

21. The prescription dispensing system as set forth in claim 1 wherein the remote location is a central pharmacy center, said pharmacist at the central pharmacy center having access to the patient medication record corresponding to a prescription to be dispensed and having access to the webcams to verify the type and amount of medication dispensed.

22. The prescription dispensing system as set forth in claim 21 wherein the healthcare professional supplies biometric information to the dispensing station corresponding to the potential prescription medication recipient, said dispensing station including means for comparing said biometric information to an output of the biometric reader before dispensing medication.

23. The prescription dispensing system as set forth in claim 21 wherein the central pharmacy center has access to a plurality of dispensing stations located at different locations.

24. The prescription dispensing system as set forth in claim 1 wherein the biometric reader is a fingerprint reader.

25. The prescription dispensing system as set forth in claim 1 wherein the webcams allow communication between the potential prescription medication recipient and the pharmacist at the remote location.

26. The prescription dispensing system as set forth in claim 1 wherein the healthcare personnel introduces the potential prescription medication recipient to the pharmacist via the secure interne connection, at least one of said webcams being usable by the pharmacist to allow identification of the person at the dispensing station.

27. The prescription dispensing system as set forth in claim 26 wherein at some of the webcams, microphone and speakers allows the potential medication recipient to ask questions and provide visual images to the pharmacist for medication-related issues and receive verbal and visual instructions from the pharmacist sufficient to satisfy state board of pharmacy regulations regarding pharmacist counseling and provision of drug information within the state where the dispensing station is located.

28. The prescription dispensing system as set forth in claim 26 wherein the prescription is transmitted electronically by completing a web-based form.

29. The prescription dispensing system as set forth in claim 26 wherein a webcam is disposed at dispensing station to receive a copy of potential prescription medication recipient documentation for payment, including third-party cards or forms, credit cards or debit cards.

30. The prescription dispensing system as set forth in claim 26 further including a smart card reader attached to the dispensing station for receiving payment cards electronically.

31. The prescription dispensing system as set forth in claim 30 wherein the payment card is selected from the group consisting of third-party payment cards, credit cards, or debit cards.

32. The prescription dispensing system at set forth in claim 26 further including a printing system designed to deliver printed material regarding the dispensed medication as required by state board of pharmacy regulations within the state where the dispensing station is located.

33. The prescription dispensing system as set forth in claim 1 wherein the potential prescription medication recipient is a patient.

34. The prescription dispensing system as set forth in claim 1 wherein the potential prescription medication recipient is an authorized caregiver for a patient.

35. The prescription dispensing system as set forth in claim 34 wherein the healthcare professional authorizes use of the dispensing station by the authorized caregiver or patient, said pharmacist authorizing dispensing of medication from said dispensing station to said authorized caregiver or patient.

36. The prescription dispensing system as set forth in claim 1 wherein the transfer of patient information by the system satisfies governmental privacy regulations such as HIPAA privacy regulations.

37. The prescription dispensing system as set forth in claim 1 wherein the prescription is in electronic format, the system being responsive to receipt of a prescription in electronic format to verify the prescription and dispense the prescribed medication.

38. The prescription dispensing system as set forth in claim 1 wherein the system includes at least three webcams, disposed in the physician office, as well as inside and outside the dispensing station, further including a microphone, monitor and speaker outside the dispensing station.

39. The prescription dispensing system as set forth in claim 1 wherein at least some of the prescription medications held in inventory are contained in barcoded containers specific to each medication.

40. The prescription dispensing system as set forth in claim 39 further including barcoded modules containing an updateable, specified combination of medication containers for said dispensing station's inventory.

41. The prescription dispensing system as set forth in claim 1 further including means for comparing the image of dispensed medication with a database of correct images for said medications, and means for comparing the medication prescribed with a patient prescription record as entered by healthcare personnel in the physician's office or by pharmacy personnel at the pharmacy distribution center.

42. The prescription dispensing system as set forth in claim 41 further including apparatus for counting out the prescribed medication, transferring said medication to the vial, applying a label to the vial, and transferring the visually inspected container to the prescription medication recipient, under visual monitoring by the pharmacy personnel via one of said webcams.

43. The prescription dispensing system as set forth in claim 1 further including a magnetic card reader disposed at the dispensing station for reading cards selected from the group consisting of smart cards, payment cards, and third-party reimbursement cards.

44. The prescription dispensing system as set forth in claim 1 further including a webcam, microphone, barcode reader, computer and monitor for the pharmacy personnel at the remote location for allowing visual and barcode verification of all barcoded containers, visual verification of the medication, container and labeling, and visual and verbal verification of the patient/customer, physician and written documentation.

45. A prescription dispensing system comprising:
- a dispensing station for holding an inventory of prescription medications;
- a secure internet connection to the dispensing station for access by a potential prescription medication recipient, by healthcare personnel in a physician office and by pharmacy personnel at the pharmacy distribution center in a remote location;
- at least two webcams for visual and auditory communication between the location of the dispensing station and the pharmacy personnel via the internet to allow identification of the correct medication, identification and communication with the correct potential prescription medication recipient, and visual validation and recording of all documentation from the physician's office or potential prescription medication recipient;
- a biometric reader disposed at the dispensing station for identifying a potential prescription medication recipient, said biometric reader being connected via the secure internet connection to the remote location, wherein the dispensing station inventory of prescription medications is held in a removable module, said module being refillable at a central pharmacy location.

46. A prescription dispensing system comprising:
- a dispensing station for holding an inventory of prescription medications;
- a secure internet connection to the dispensing station for access by a potential prescription medication recipient, by healthcare personnel in a physician office and by pharmacy personnel at the pharmacy distribution center in a remote location;
- at least two webcams for visual and auditory communication between the location of the dispensing station and the pharmacy personnel via the internet to allow identification of the correct medication, identification and communication with the correct potential prescription medication recipient, and visual validation and recording of all documentation from the physician's office or potential prescription medication recipient;
- a biometric reader disposed at the dispensing station for identifying a potential prescription medication recipient, said biometric reader being connected via the secure internet connection to the remote location, wherein the healthcare personnel introduces the potential prescription medication recipient to the pharmacist via the secure internet connection, at least one of said webcams being usable by the pharmacist to allow identification of the person at the dispensing station wherein at least one of the webcams is disposed in the physician office for use in transmitting an official copy of the written prescription.

* * * * *